United States Patent [19]

Staehlin et al.

[11] Patent Number: 5,704,938

[45] Date of Patent: Jan. 6, 1998

[54] IMPLANTABLE BONE LENGTHENING APPARATUS USING A DRIVE GEAR MECHANISM

[75] Inventors: John H. Staehlin, Lutherville; Gary L. Segal, Ellicott City; David King, Elkton; Guy Rubley, Arbutus; Dror Paley, Baltimore, all of Md.

[73] Assignee: Volunteers For Medical Engineering, Baltimore, Md.

[21] Appl. No.: 624,920

[22] Filed: Mar. 27, 1996

[51] Int. Cl.⁶ .................................................. A61B 17/56
[52] U.S. Cl. ..................... 606/62; 606/63; 606/86; 606/105; 606/57; 606/58
[58] Field of Search ........................ 606/62, 63, 72, 606/86, 105, 57, 58

[56] References Cited

U.S. PATENT DOCUMENTS

| | | |
|---|---|---|
| 4,946,459 | 8/1990 | Bradshaw et al. . |
| 5,074,882 | 12/1991 | Grammont et al. . |
| 5,350,379 | 9/1994 | Spievack . |
| 5,387,239 | 2/1995 | Bianco et al. . |
| 5,415,660 | 5/1995 | Campbell et al. . |
| 5,505,733 | 4/1996 | Justin et al. .............................. 60/105 |

Primary Examiner—Michael Buiz
Assistant Examiner—Daphna Shai
Attorney, Agent, or Firm—Finnegan, Henderson, Farabow, Garrett, & Dunner, L.L.P.

[57] ABSTRACT

A bone lengthening mechanism is placed into a bone which is then lengthened by extending the mechanism. The mechanism is extended by effecting a rotational movement in a drive bolt which mates with a threaded portion in a section of the mechanism. The threads convert the rotational movement to a longitudinal force thereby lengthening the bone.

7 Claims, 5 Drawing Sheets

IMPLANTABLE BONE LENGTHENING APPARATUS USING A DRIVE GEAR MECHANISM

BACKGROUND OF THE INVENTION

1. Field of the Invention

This invention relates to apparatus used in the field of orthopedic surgery, in general, and, more specifically, to apparatus used in the field of bone lengthening surgical procedures.

2. Description of the Related Art

The typical apparatus used for the bone lengthening procedure consists of a special nail implanted in the hollowed-out cavity formed by the removal of the bone marrow from, for example, a leg bone, and an external longitudinally-adjustable frame assembly, one end of which is secured to one end of the bone to be lengthened and the other end of which is attached to the other end of the bone and to the nail. The bone is then broken and this adjustable frame is periodically lengthened causing the bone, as the break is knitting, to also lengthen. This external frame fixation system is difficult to securely locate on the patient, resulting in discomfort and an unattractive appearance. More seriously, the pins being secured in the bone and protruding outside of the skin increase the risk of infection. Thus, there is a need for a bone lengthening device which incorporates a jacking action into the structure of the implantable nail body, thereby eliminating the need for this external frame and all of its related problems.

SUMMARY OF THE INVENTION

Accordingly, the present invention is directed to a totally implantable apparatus which will force one end of a broken bone away from the other end while maintaining the bone sections in alignment during the procedure.

Additional features and advantages of the invention will be set forth in the description that follows, and, in part, will be apparent from the description, or may be learned by the practice of the invention. The features and/or other advantages of the invention will be realized and attained by the apparatus, particularly pointed out in the written description and claims hereof, as well as in the appended drawings.

To achieve these and other advantages in accordance with the purpose of the invention, the invention includes an apparatus for lengthening bones, the apparatus including a means for activating a lengthening mechanism which is physically located within the structure of the apparatus from outside the patient.

In another aspect, the invention also allows for adjustment of implantable bone lengthening apparatus which will automatically and periodically adjust the length of the apparatus on a scheduled basis over the entire procedure. This feature will provide the optimum lengthening/bone knitting sequences to minimize the overall length of time it takes for the entire procedure to be completed.

It is to be understood that both the foregoing general description and the following detailed description are exemplary and explanatory, and are not restrictive of the invention as claimed.

BRIEF DESCRIPTION OF THE DRAWING

The accompanying drawings, which are incorporated in and constitute a part of this specification, illustrate embodiments of the invention and, together with the description, serve to explain the objects, advantages, and principles of the invention.

In the drawings.

DETAILED DESCRIPTION OF THE PREFERRED EMBODIMENTS

Figure 3:
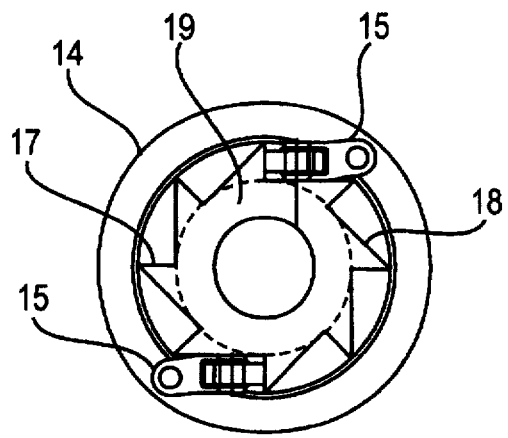
FIG. 3 is a horizontal cross-section view of the ratchet drive mechanism along line A in FIG. 1.
Figure 1:
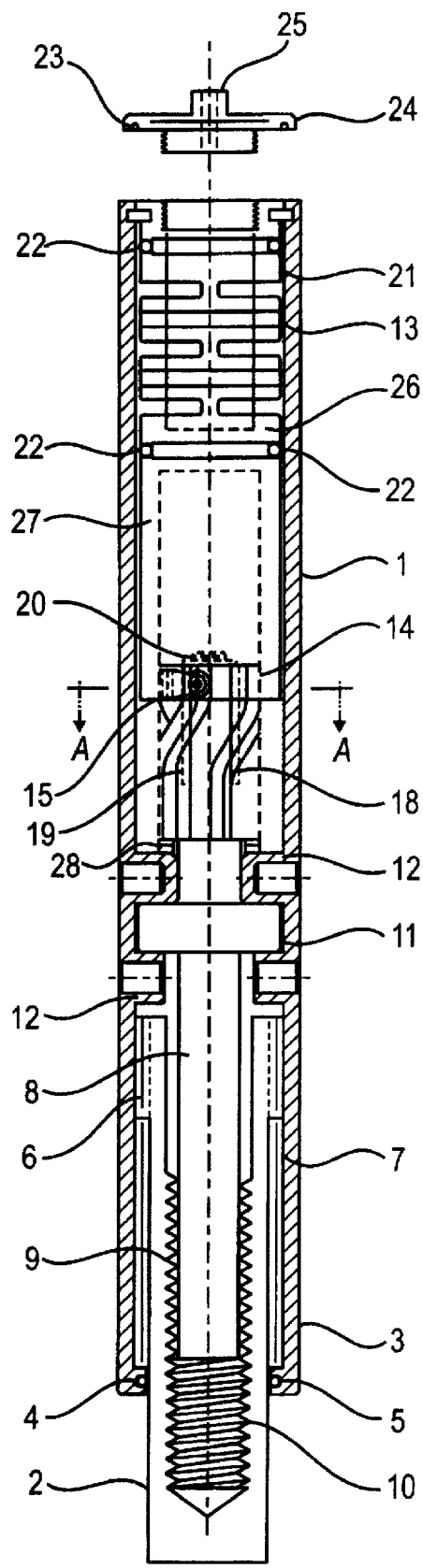
FIG. 1 is a cross-section view of the implantable bone lengthening apparatus.
Figure 2:
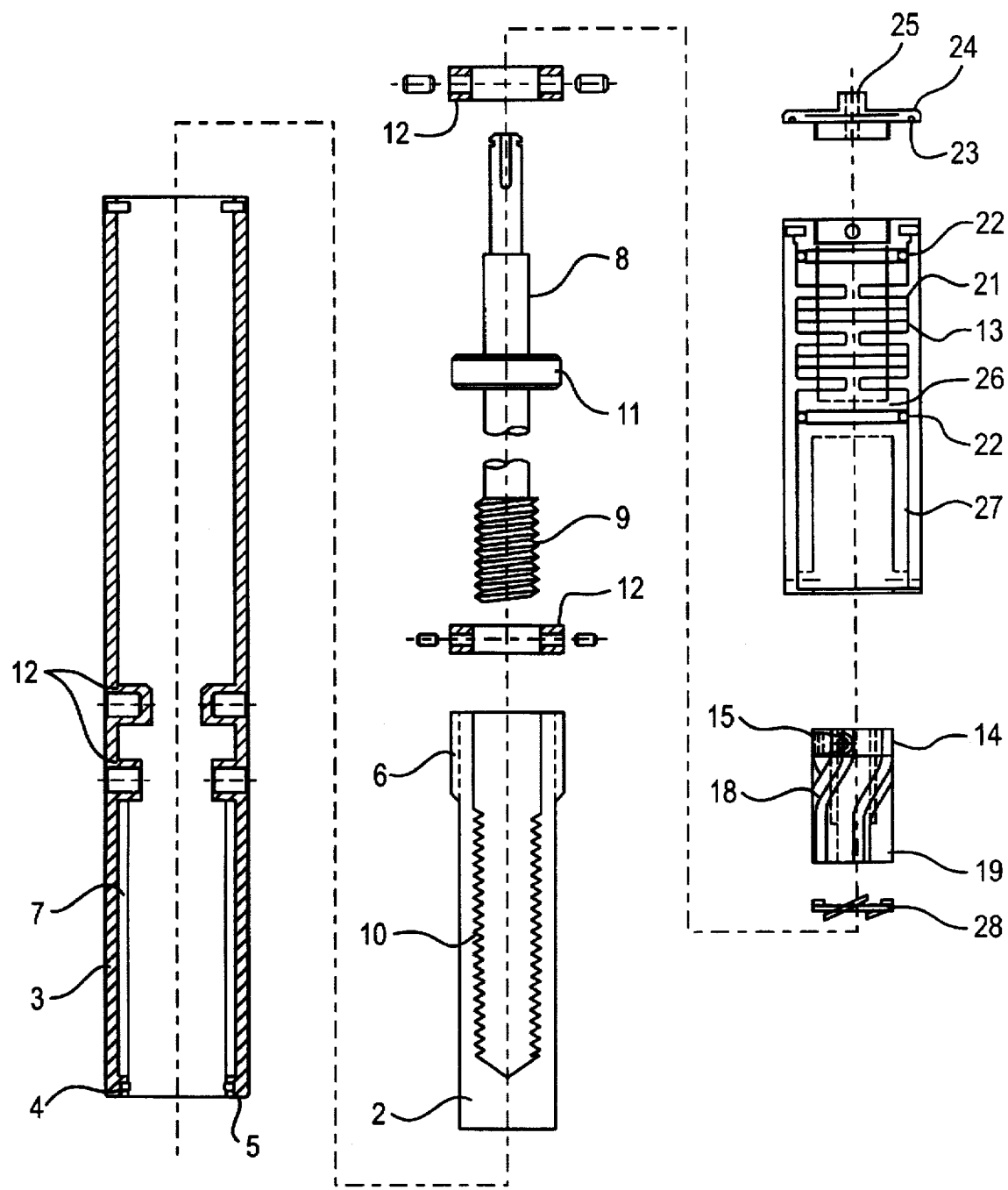
FIG. 2 is an exploded, cross-section view of implantable nail assembly.
Figure 4:
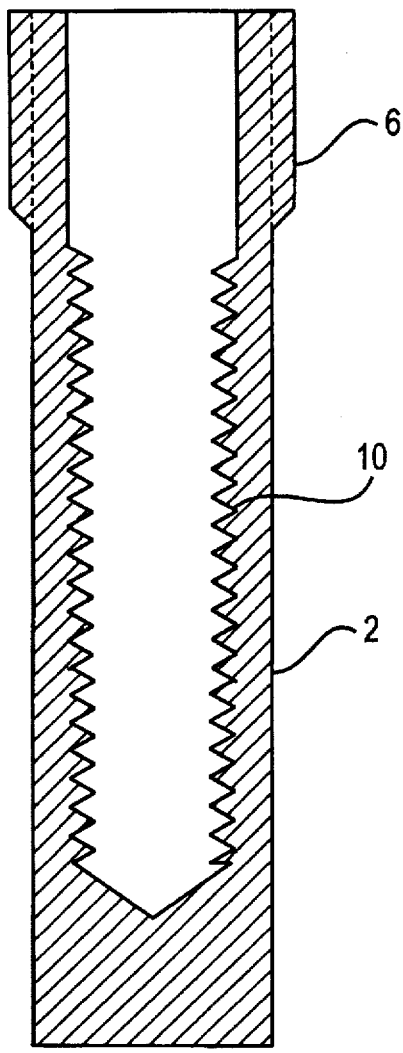
FIG. 4 is a cross-section view of the first nail section body of the implantable bone lengthening apparatus.
Figure 5:
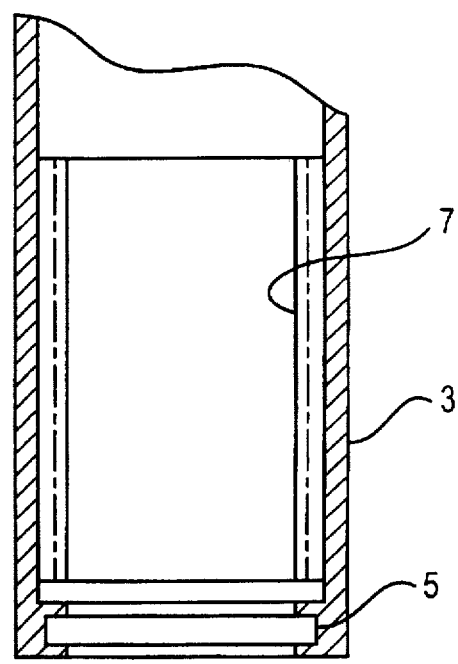
FIG. 5 is a cross-section view of the lower portion of the second nail section body of the implantable bone lengthening apparatus.
Figure 6:
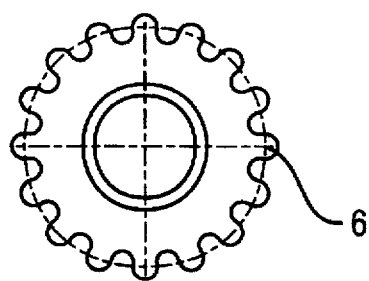
FIG. 6 is a horizontal cross-section view of the upper portion of the first nail section body of the implantable bone lengthening apparatus.
Figure 7:
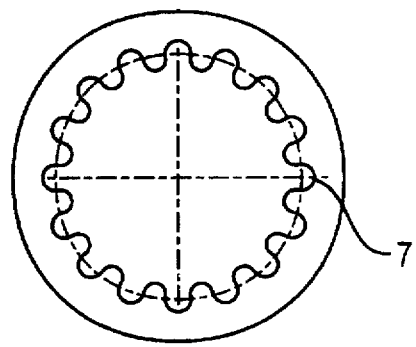
FIG. 7 is a horizontal cross-section view of the lower portion of the second nail section body of the implantable bone lengthening apparatus.

In a first embodiment illustrated in FIGS. 1 and 2, the bone lengthening apparatus 1 consists of a first nail section body 2 whose outside diameter matches the inside diameter of a cavity in the bone marrow of the section of a limb to be lengthened (not shown) and a second nail section body 3. The first nail section body 2 is slidably received in the second nail section body 3 through an "O" ring seal 4 located in a recess 5 at the end of the second nail section body 3. The upper section the first nail section body 2 has an increased outside dimension and has external splines 6 which mate with internal splines 7 of the second nail section body 3. The splines are shown in more detail in FIGS. 4–7.

The first nail section body 2 is the leading section and has a rounded tip (not shown) and enters the bone marrow cavity first. The second nail section body 3 is also configured to be implanted in a bone marrow cavity and houses a drive mechanism which, in this embodiment, includes a drive bolt 8 having an externally-threaded section 9 which engages the internally-threaded bore 10 of the first nail section body 2. This drive bolt 8 transmits the torque of the drive mechanism to the first nail section body 2 where the torque is converted into a longitudinal force in the internally threaded bore 10. In this configuration, the drive bolt 8 is allowed to freely rotate in the first nail section body 2. The longitudinal force in the drive bolt 8 is projected by the shoulder 11 on the drive bolt 8 reacting against bearing surfaces 12 fixed to the inside bore of the second nail section 3. The external splines 6 of the first nail section body 2 react against the internal splines 7 of the second nail section body 3 thereby assuring that the sections do not rotate relative to one another when the apparatus is extending.

According to one embodiment, the drive mechanism is a rotating ratcheting mechanism which may be used to rotate the drive bolt 8. The ratcheting mechanism of the preferred embodiment includes a longitudinally translating plunger assembly 13. The plunger assembly 13 is connected to an articulated roller assembly 14 having rollers 15 which are biased by springs 16 to turn in toward the center of the drive bolt 8. See FIG. 8. The rollers 15 engage a flat surface section 17 of generally longitudinally extending helical splines 18 formed on a helical toothed index drive 19. The helical toothed index drive 19 is rigidly attached to the drive bolt 8 so that the drive bolt rotates with the helical toothed index drive 19. The roller assembly 14 generally surrounds the helical toothed index drive 19 and is kept from sliding off of one end the helical toothed drive by a retaining ring 20.

A machine spring 21 having sealing "O" rings 22 is fitted into the an upper part of the second nail section body 3, which is sealed off by an "O" ring 23 fitted end cap 24. The end cap 24 has a fluid port 25 extending therethrough. The fluid port is connected to an outside source of fluid (not shown) which is implanted under the skin by a tube (not shown) which extends through a hole drilled in the bone. The outside fluid source may also be outside of the skin, in which case, the tube extends out through an incision in the skin.

Pressurized fluid is forced through the port 25 and pushes against a plunger 26 rigidly attached to the bottom of the machine spring 21 and forces it to translate longitudinally relative to the second nail section body 3. The lower portion of the plunger assembly is a generally tubular member 27 which attaches to the roller assembly 14 and surrounds the helical toothed index drive 19 as the plunger translates.

Figure 8:
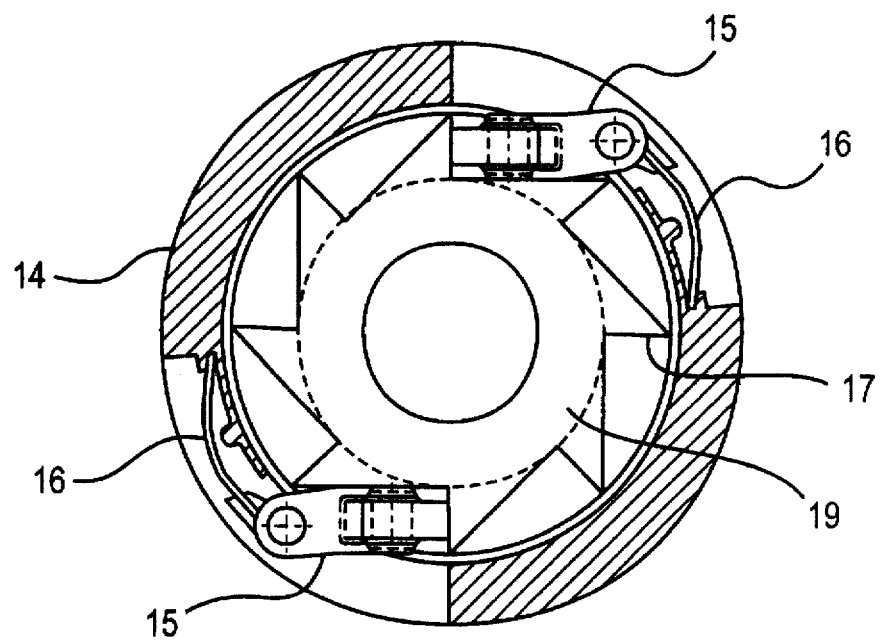
FIG. 8 is a horizontal cross-section view of the ratchet drive mechanism in its driving position.
Figure 9:
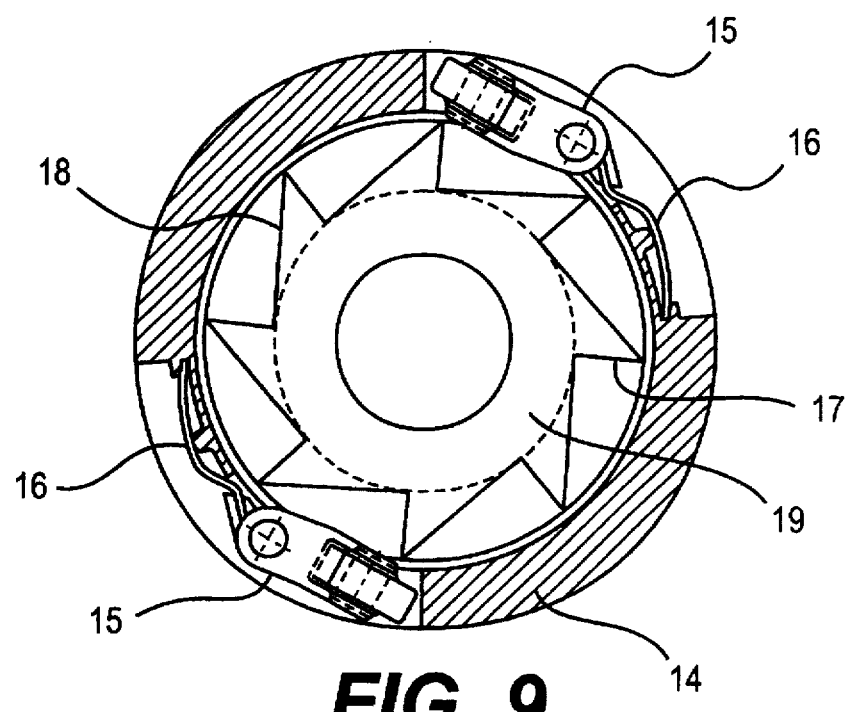
FIG. 9 is a horizontal cross-section view of the ratchet drive mechanism in its retracting position.
Figure 10:
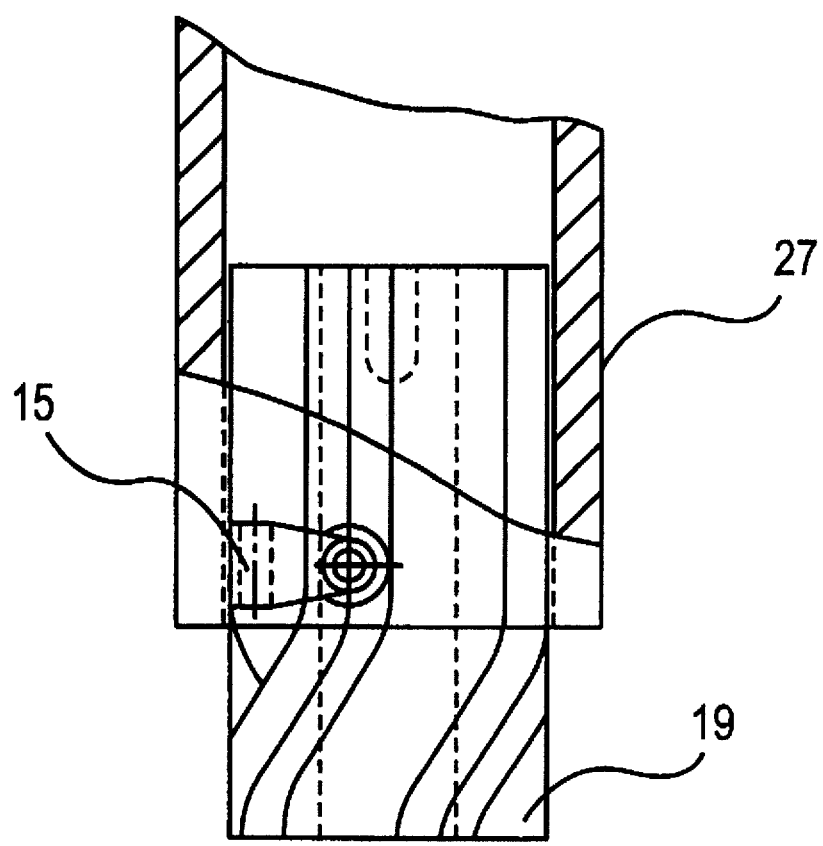
FIG. 10 is a cross-sectional view of the ratchet drive mechanism driving the helical toothed index drive.

As the assembly moves longitudinally, the interaction of the rollers 15 against the flat surfaces 17 of the helical splines 18 causes the drive bolt 8 to rotate. This interaction is illustrated in FIGS. 8 and 10. The rotation of the drive bolt 8 causes the lower section body 2 to move longitudinally due to the interaction of the threads 9 on the drive bolt 8 and the internally threaded bore 10.

The helical toothed index drive is prevented from rotating in the opposite direction by a ratchet device. An acceptable ratchet device may include a split metal washer 28 which is located between the upper surface of the upper-most bearing surface 12 and the bottom of the helical toothed index drive 19. The split metal washer interacts either with the helical splines or a serrated bottom surface of the helical toothed index drive to prevent the helical toothed index drive from rotating in the direction opposite to the driven direction.

When the pressurized fluid is removed through the fluid port 25, the extended machine spring 21 retracts the roller assembly. When the roller assembly is retracted, the helical toothed index drive remains stationary because of the ratchet device. Each roller rides up and over the helical spline adjacent to the helical spline just driven thereby causing the articulated spring-loaded rollers to move radially out from the longitudinal axis of the drive bolt 8. After each roller rides up and over the helical spline, it is forced by the spring into or near the area of the flat surface section 17 of the helical spline it had just ridden over. It is now ready for the next longitudinal translation of the plunger.

There are numerous means for application of this pressurized fluid to the port 25 either from a source external or internal to the implanted bone lengthening mechanism. An example of such a pressurizing source is described in copending U.S. patent application Ser. No. 08/562,872 titled "Implantable Bone lengthening Apparatus" to Staehlin et al., filed Nov. 27, 1995 which is expressly incorporated herein in its entirety by reference.

It will be apparent to those skilled in the art that various modifications and variations can be made in the disclosed process and product without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A bone lengthening nail assembly comprising:
   a first nail section body;
   a second nail section body which slidably receives said first nail section body;
   a drive bolt located in said second nail section body and extending into said first nail section body;
   a rotating drive mechanism operatively connected to the drive bolt and located in said second nail section body for rotating said drive bolt to move the first nail section body relative to the second section body; and
   at least one roller assembly in contact with a surface of a generally longitudinally extending helical spline and a longitudinally translating member for imparting a longitudinal force to said at least one roller assembly and causing said drive bolt to rotate.

2. The bone lengthening nail of claim 1, wherein said longitudinally translating member is a plunger, and said assembly further comprises:
   a pressurized fluid source connected to said second nail section body which forces pressurized fluid into said second nail thereby causing said plunger to longitudinally translate.

3. The bone lengthening nail of claim 1, further comprising:
   a machine spring located in said second nail section body for retracting said longitudinally translating member after said drive bolt is rotated.

4. The bone lengthening nail of claim 3, further comprising a ratchet device which prevents the drive bolt from rotating in the direction opposite to the drive direction.

5. The bone lengthening device of claim 4, wherein said ratchet device is a split metal washer.

6. The bone lengthening nail of claim 1, further comprising:
   splines located on said first and second nail section bodies which prevent said first and second section bodies from rotating relative to each other.

7. The bone lengthening nail of claim 1, further comprising:
   threads located on said drive bolt which mate with threads located in either of said first or second nail section bodies so that the rotation of the drive bolt is converted to a longitudinal force, thereby causing said first nail section body to move relative to said second nail section body.

\* \* \* \* \*